United States Patent [19]

Beaty et al.

[11] Patent Number: 5,312,329
[45] Date of Patent: May 17, 1994

[54] PIEZO ULTRASONIC AND ELECTROSURGICAL HANDPIECE

[75] Inventors: Michael A. Beaty; Arlan J. Reschke, both of Boulder; Robert B. Stoddard, Louisville; Jon P. Page, Broomfield; Bandele Jeffrey-Coker, Westminster; Michael Olichney, Boulder, all of Colo.; Emery S. Rose, New York, N.Y.

[73] Assignee: Valleylab Inc., Boulder, Colo.

[21] Appl. No.: 44,430

[22] Filed: Apr. 7, 1993

[51] Int. Cl.$^5$ .............................................. A61B 17/32
[52] U.S. Cl. ......................................... 604/22; 601/2
[58] Field of Search ................. 604/22; 606/169–171, 606/38, 40; 128/24 AA

[56] References Cited

U.S. PATENT DOCUMENTS

| | | | |
|---|---|---|---|
| 4,674,498 | 6/1987 | Stasz | 604/22 |
| 4,741,731 | 5/1988 | Starck et al. | 604/22 |
| 4,751,916 | 6/1988 | Bory | 128/24 AA |
| 4,804,364 | 2/1989 | Dieras et al. | 604/22 |
| 4,861,332 | 8/1989 | Parisi | 604/22 |
| 4,886,060 | 12/1989 | Wiksell | 604/22 |
| 4,903,696 | 2/1990 | Staez et al. | 604/22 |
| 4,931,047 | 6/1990 | Broadwin et al. | 604/22 |
| 4,978,333 | 12/1990 | Broadwin et al. | 604/22 |
| 5,015,227 | 5/1991 | Broadwin et al. | 604/22 |
| 5,178,605 | 1/1993 | Imonti | 604/22 |
| 5,190,517 | 3/1993 | Zieve et al. | 604/22 |

Primary Examiner—C. Fred Rosenbaum
Assistant Examiner—Michael Rafa
Attorney, Agent, or Firm—Peter C. Richardson; Lawrence C. Akers; Aaron Passman

[57] ABSTRACT

An ultrasonic and electrosurgical handpiece housing has an axis, a distal end, a proximal end and a passage defined by an inside wall. A piezo stack has elements carried along a plane generally transverse to the axis. A retainer for the elements has distal, intermediate and proximal portions. The distal portion has a fastener; the proximal portion has a threaded shoulder bolt. The stack about the shoulder has an energy input and a reference output positioned axially apart from one another. An insulating sleeve about the bolt is between central openings of the elements and the bolt. A pair of insulators about the bolt has the stack therebetween; one insulator is between the plane and the stack and the other is near the threads. The intermediate portion attaches to the housing at the plane with decoupling and sealing. An irrigation channel conveys fluid. The drive energy input, the feedback signal and the reference outputs are insulated by the sleeve and pair from the bolt. A washer against the insulator and about the threads applies axial but not torsion to the insulator when a clamping nut on the threads holds components on the bolt. The clamping nut is in circuit with electrosurgical energy as the reference return for electrosurgery. A tool fastens to a connector for transmitting axial vibrations in the form of a predefined stroke at a tip thereof.

26 Claims, 7 Drawing Sheets

PIEZO ULTRASONIC AND ELECTROSURGICAL HANDPIECE

FIELD OF THE INVENTION

A piezo ultrasonic and electrosurgical handpiece construction, with insulation between the energy inputs for ultrasonic driving and electrosurgery, permits vibration along its axis and fluid irrigation without shorting. A replaceable structure for the umbilical cord has a connector at each end which conjugate with the handpiece and the generators.

BACKGROUND OF THE DISCLOSURE

Ultrasonic and electrosurgical handpieces of various configurations to facilitate their usefulness and reliability have been used for a variety of surgical procedures. The combination of an electrosurgical and ultrasonic handpiece presents an number of challenges and problems. The most notable difficulty is the isolation of the radio frequency energy from the ultrasonic driving energy.

The handpiece requires a compact design that is facilitated by a piezo driver for the ultrasonic vibration. The use of piezo crystals such as barium titanate or lead titanate zirconate to drive the tool at ultrasonic frequencies is known in an Ultra product sold by Sharplan Laser and is manufactured by Fibrasonics Inc. That product is merely an ultrasonic tool with air cooling and without electrosurgical high frequency cutting and/or coagulation.

U.S. Pat. No. 4,674,498 has an electrosurgical system in which a blade is made to vibrate at a frequency sufficient to cause cavitation to take place as RF energy is simultaneously applied to electrodes on the blade for effecting cutting or coagulation. U.S. Pat. NO. 4,886,060 has an ultrasonic knife including high frequency electric coagulation. Cardiac floating isolation for the ultrasonic aspirator enables monopolar coagulation with the handle therefore as a completely passive conductor. The insulation circuit of the ultrasonic knife has specific dimensions to withstand RF energy to earth. Protecting the user with such circuitry neglects the preferred double insulation technique for maximum protection and double insulation has not been disclosed in the prior patents.

U.S. Pat. No. 4,903,696 has a generator that powers the electrodes of electrosurgical implements and at the same time the ultrasonic transducer for imparting vibratory motion to such implements.

U.S. Pat. No. 4,931,047 has a solution to incorporating a RF coagulating and RF cutting capability with a vibrating tip of an ultrasonic aspiration and fragmentation device. Switching is provided for the surgeon to use RF and/or ultrasonic as desired and without need of changing the surgical instrument. Insulation of the piezo driver from the high frequency electrosurgical energy is not known or in the devices available since the use of high dielectric electrical insulators in an ultrasonic transducer includes stress and structural problems heretofore unsolved.

SUMMARY OF THE INVENTION

A piezo ultrasonic and electrosurgical handpiece preferably has a housing being elongated along its axis with a distal end, a proximal end and a passage therethrough. A piezo transducer may have a plurality of elements supported within the housing and mounted along a plane generally transverse to the axis of the housing and the passage therealong.

A retainer for the piezo elements most preferably has a distal portion, intermediate portion and a proximal portion. The distal portion may have a fastener positioned near the distal end of the housing. The proximal portion most preferably has an extended mandrel in the form of a shoulder bolt with proximally disposed threads. The intermediate portion attaches to the housing with provisions for locating the retainer axial with respect thereto with decoupling therebetween.

A stack of components are the piezo elements and feedback crystal wherein each component most preferably has a centrally located hole and an energy input and a reference output positioned axially apart from one another. The stack assembles on the shoulder bolt and is positioned with the holes thereabout.

An insulating sleeve is most preferably disposed about the shoulder and sandwiched between the central openings of the stack and the shoulder of the bolt. A pair of insulators preferably may be disposed about the retainer with the stack positioned between the insulators as a sandwich. One of the pair of insulators is between the plane and the stack, and the other insulator is adjacent the threads and against the stack so an ultrasonic drive energy connected in circuit with the energy input of the elements. The feedback signal and reference output in the stack are insulated by the sleeve and pair from the shoulder bolt.

A washer against the insulator and about the threads is most preferably in position to apply axial but not torsional loads on the insulator and stack therebeneath. A clamping nut is most preferably proximally located on the threads to hold the washer axially against the components on the shoulder bolt. The clamp nut is most preferably for receiving an electrical source of electrosurgical energy for electrosurgical cutting or coagulating and is isolated from the piezo circuit. The plane of the retainer is most preferably arranged at a node point of the axial reciprocatory motion.

A tool may connect to the fastener with a complimentary connector and it is held thereto for transmitting axial vibrations in the form of a predefined stroke therealong to a tip thereof. The tool may include an axis aligned with the axis of the retainer for the stack. The housing passage has an inside wall and the retainer includes sealing provisions with respect to the inside wall of the housing. The retainer most preferably has an axial passageway therethrough allowing fluid flow to pass without fluid communicating with the electrical connections of the stack.

A fastener connects to a hollow tubular tool and has a bore therethrough located along an axis thereof. The bore most preferably is in fluid communication with an axial passageway through the retainer. An irrigation channel may be provided within the housing and is segregated from the stack for conveying irrigation fluid at the distal end of the housing. A flue conjugated with the distal end of the housing. The irrigation channel is most preferably in fluid communication with the flue and may be supported about the distal end of the housing concentric with respect to the tool. Irrigation fluid passes within an annular space around the tool but inside of the flue to transmit fluid to the tool end away from the housing.

A passageway through the retainer connects to a vacuum source to provide suction at the tool end. A juncture between the tool and the fastener may preferably be in an alternate embodiment at an angle such that the axis of the passage through the retainer and an axis of the tool are at an obtuse angle. A washer between the nut and stack may be adapted to be held against twisting during tightening of the clamping to an axial preload that stretches the shoulder bolt so the stack is held under a predetermined compression.

A voltage potential between the feedback signal and the reference output indicates the particular feedback crystal in the handpiece. An adjustable resistance is most preferably located in series with the feedback signal being calibrated to a preset value so that the stack can be used with any source of ultrasonic energy. A tool may be selected to be interchangeable with other tools of different lengths and configurations and the operation will be maintained. Specifically, the adjustable resistance most preferably is capable of calibrating different tools so the stack and source of energy accommodates the tools. The stroke at the tip of the tool is most preferably uniform.

A stack acting as a capacitor and bleed resistors are most preferably connected in parallel across and in circuit with the energy input of the elements, feedback signal and reference output, respectively, to provide electrical discharge.

Controls may be on an outside surface of the housing for controlling electrosurgical energy, ultrasonic drive energy, and irrigation. A flat ribbon of wires most preferably connects the energy input of the elements, feedback signal and reference output. These are supplied to the handpiece by an insulated three wire ribbon cable with the reference output amid the energy input and feedback output.

The insulated three wire ribbon cables may have a strain relief where it is connected to a connector block. A removable attachment to an ultrasonic generator and the wires terminate at the connector block. A first slotted keeper preferably retains a serpentine length of ribbon cable and a second keeper retains the first keeper. The connector block to terminate the wires is in circuit with the controls. The ultrasonic drive energy and the reference output and feedback signal connect to an ultrasonic generator and an electrosurgical generator by a cable from the connector block to the electrosurgical generator when the connector block is plugged into a receiving terminal on the ultrasonic generator.

A manifold interconnects with the proximal end and a floating fitting disposed therebetween preferably permits movement of the fitting to center and seal fluid flow to the irrigation channel.

DETAILED DESCRIPTION OF THE INVENTION

Figure 1:
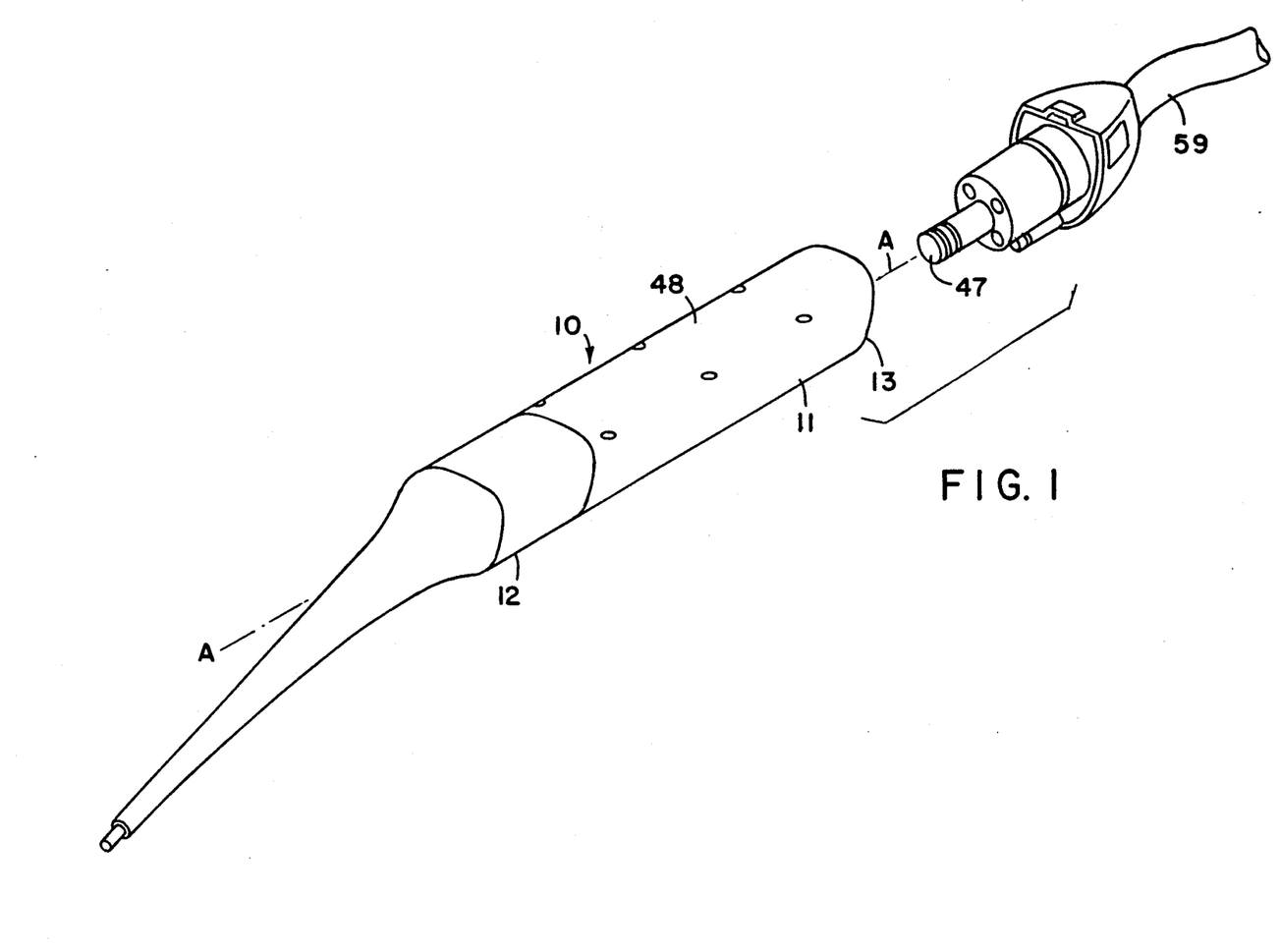
FIG. 1 is a perspective view of a piezo ultrasonic and electrosurgical handpiece shown with its umbilical cord separated as in an exploded view.
Figure 2:
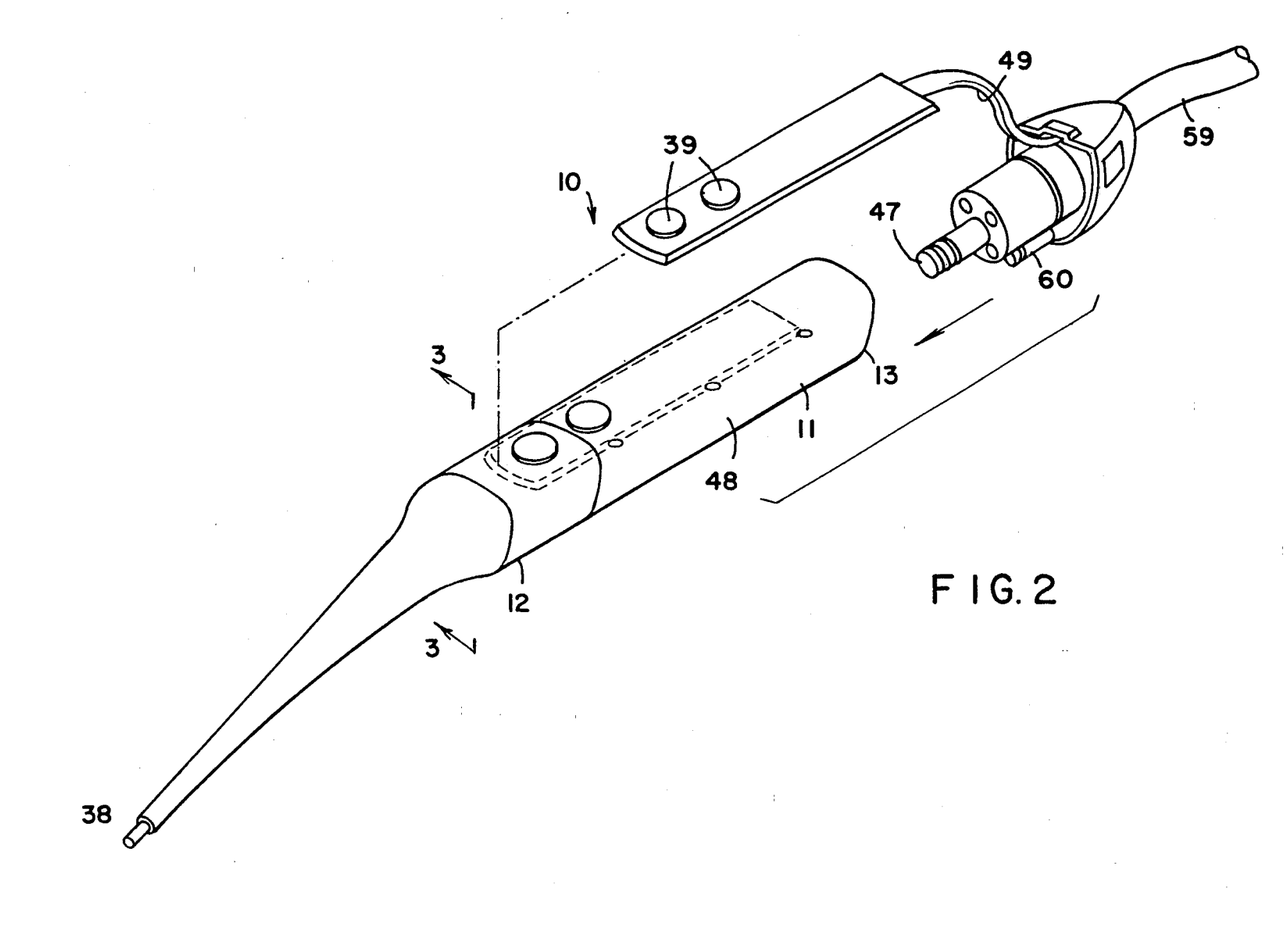
FIG. 2 is a perspective view similar to FIG. 1 but the separated umbilical cord is shown with the switch control in position for attachment to the housing of the piezo ultrasonic and electrosurgical handpiece.

A piezo ultrasonic and electrosurgical handpiece 10 is illustrated in perspective in FIGS. 1 and 2. The handpiece 10 has a housing 11 made of an insulating plastic into an elongated hollow shell. The longer dimension of the housing 11 aligns along its axis "A" with a distal end 12 and a proximal end 13. A piezo transducer 15 formed of crystals includes a plurality 16 of elements supported within the housing 11 and carried in a plane 17 generally transverse to the axis "A" of the housing 11 and the passage 14 therealong.

Figure 3:
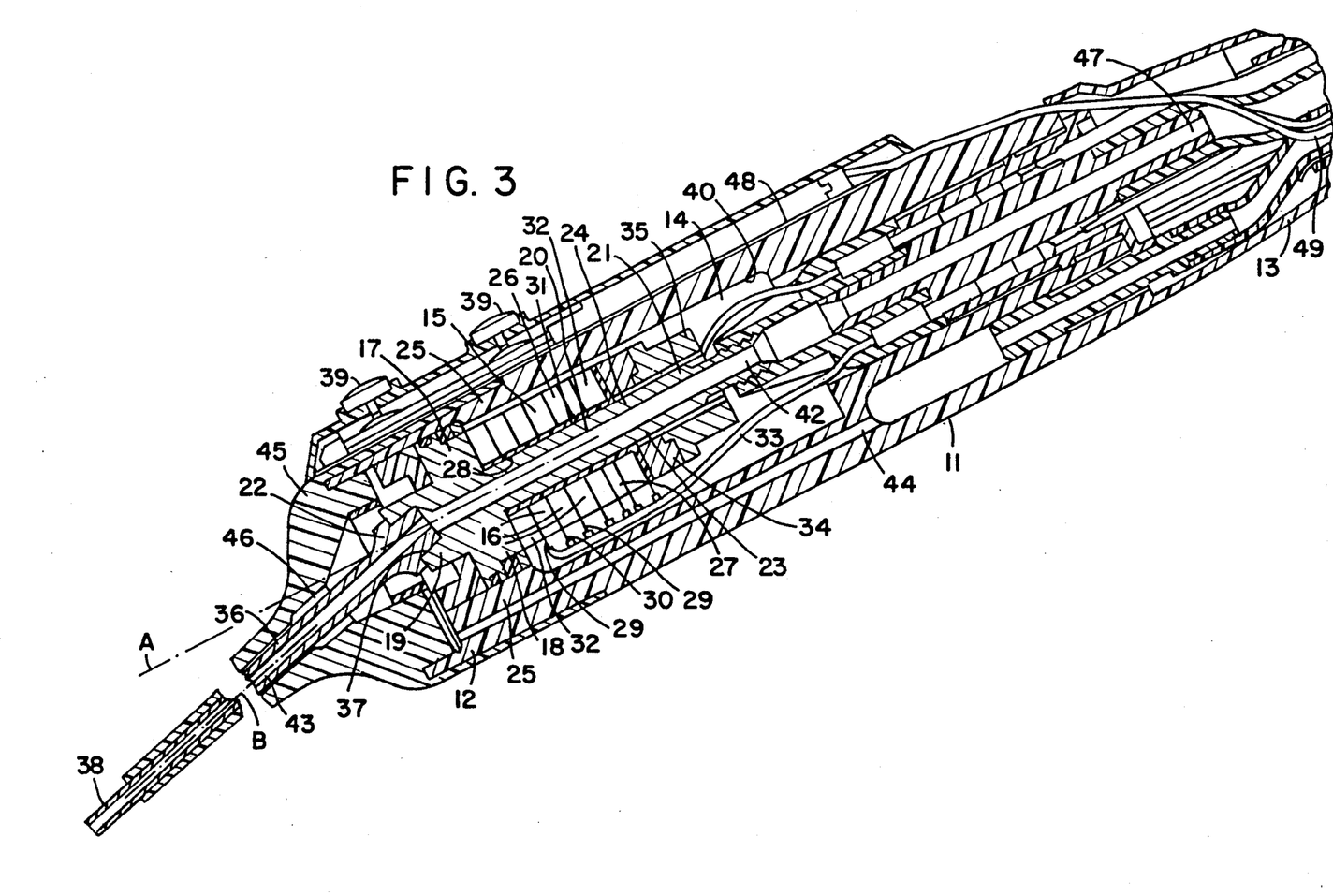
FIG. 3 is a side view in cross section as would be seen if taken along line 3—3 of FIG. 2 and if the exploded umbilical cord and switch thereof were full assembled to the piezo ultrasonic and electrosurgical handpiece.

A retainer 18 in FIG. 3, a cross section along lines 3—3 in FIG. 2, for the piezo crystal elements 16 has a distal portion 19, intermediate portion 20 and a proximal portion 21. The distal portion 19 may have a fastener 22 (not specifically shown but typically fine threads) positioned near the distal end 12 of the housing 11. The proximal portion 21 has an extended mandrel 23 in the form of a shoulder bolt 24 with proximally disposed threads (not shown to avoid cluttering the Figure with unnecessary detail). The intermediate portion 20 attaches to the housing 11 at the plane 17 with provisions for locating the retainer 18 axial with respect thereto with decoupling therebetween. In particular and as shown in FIG. 3 a view of the side in cross section resilient rings 25 between the housing and the retainer 18 allow relative movement between them so the distal portion 19 can vibrate axially without interference from the housing 11, this is decoupling.

The piezo transducer 15 has a stack 26 of components which are the piezo elements 16 and a feedback crystal 27; wherein each component most preferably has a centrally located hole 28 and an energy input 29 and a reference output 30 electrically connected and positioned axially apart from one another. The stack 26 assembles on the shoulder bolt 24 and is positioned with the holes 28 of each element 16 about the shoulder bolt 24.

An insulating sleeve 31 is disposed about the shoulder bolt 24 to prevent energy in the stack 26 from grounding in the bolt 24. The sleeve 31 is sandwiched between the central holes 28 of the stack 26 and the shoulder of the bolt 24. A pair of insulators 32 disposed about the retainer 18 have the stack 26 positioned therebetween to further insulate the driving electrical energy for ultrasonic vibration. One of the pair of insulators 32 is located between the plane 17 and the stack 26, and the other insulator 32 is positioned adjacent the threads and against the stack 26 so the source of ultrasonic drive energy in the form of a wire 33 connects in a circuit to provide the energy input for stimulating the elements 16, see FIGS. 3 and 7. The feedback crystal 27 offers a signal picked up by another wire shown also in FIGS. 3 and 7. The reference output 30 from the stack 26 is a still further wire and all the wires, elements 16 and the feedback crystal 27 are insulated by the sleeve 31 and the pair 32 from the shoulder bolt 24. In FIG. 3 the routing of the wires and the positioning of the elements 16 and feedback crystal 27 are shown relative the shoulder bolt 24 and the housing 11.

A washer 34 against the insulator 32 and about the threads is in position to apply axial but not torsional loads on the insulator 32 and stack 26 therebeneath. A clamping nut 35 is proximally located on the threads to hold the washer 34 axially and tightly against the components on the shoulder bolt 24. Washer 34 between the clamping nut 35 and insulator 32 is adapted to be held against twisting during tightening of the clamping nut 35 to an axial preload that stretches the shoulder bolt 24 so the stack 26 is held under a predetermined compression.

Ultrasonic energy vibrations resulting from driving the elements 16 with is provided to the distal portion 19 and through the fastener 22 in the form of axial strokes for having excursions of about 330 micrometers and at a frequency of 23,000 hertz or 178 micrometers at 36,000 hertz at the patient contacting end of the ultrasonic electrosurgical handpiece 10. For electrosurgery, the clamping nut 35 receives a source of electrosurgical energy at up to 500,000 hertz so that cutting or coagulating can be performed with the handpiece 10. Electrical connections to the stack drive piezo elements 16 are independent of the electrosurgical energy since there is insulation 31 and 32 between the bolt 24 and the stack 26. Current flow through the piezo elements 16 and signals from the feedback crystal 27 cause controlled axial reciprocatory motion to be transmitted to the distal end 12 of the retainer 18 for conveyance to the fastener 22 thereat. The plane 17 of the retainer 18 is most preferably arranged at a node point of the axial reciprocatory motion so that the driving force of the stack 26 is not diminished.

A tool 36 as shown in FIGS. 1, 2, 3 and 4 connect to the fastener 22 with a complimentary connector 37 and it is held thereto for transmitting axial vibrations in the form of a predefined stroke therealong to a tip 38 thereof. The preferred fastener 22 and connector 37 are fine threads which are not specifically shown in FIGS. 3 or 4. The tool 36 includes an axis that may be aligned with the axis "A" of the retainer 18 as is common or at an angle to the axis "A" as is shown in the FIGS. 3 and 4. Angling the tool 36 allows it to reach difficult areas for ultrasonic and/or electrosurgery. The handpiece 10 and tool 36 are capable of either electrosurgery, ultrasonic surgery or a combination of both and switches 39 are provided for that purpose.

Figure 4:
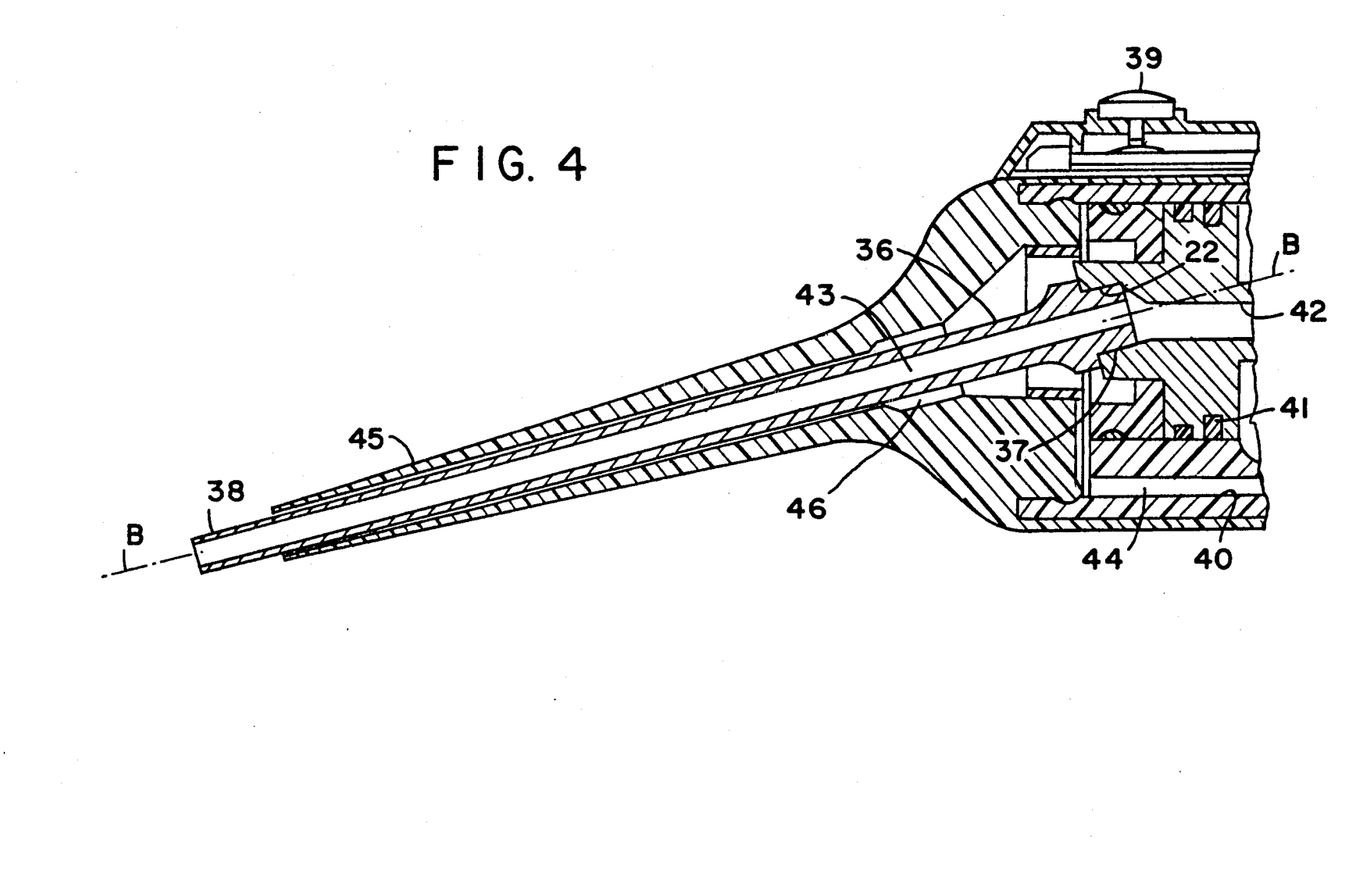
FIG. 4 is an enlarged partial view of the tool end of the piezo ultrasonic and electrosurgical handpiece shown in cross section and provided to illustrate the mounting of an angled tool.

The housing passage 14 has an inside wall 40 and the retainer 18 includes sealing provisions 41 with respect to the inside wall 40 of the housing, as shown in FIGS. 3 and 4. The retainer 18 most preferably has an axial passageway 42 therethrough allowing fluid flow to pass without any fluid communicating with the electrical connections of the stack 26.

The tool 36 is hollow and tubular with a bore 43 therethrough located along an axis "B" thereof so the bore 43 can be in fluid communication with the axial passage 42 through the retainer 18. An irrigation channel 44 provided within the housing 11 is segregated from the stack 26 for conveying irrigation fluid to the distal end 12 of the housing 11. A flue 45 conjugates with the distal end 12 of the housing 11 so the irrigation channel 44 is in fluid communication with the flue 45 which is supported about the distal end 12 of the housing 11 concentric with respect to the tool 36. Irrigation fluid thus passes within an annular space 46 around the tool 36 but inside of the flue 45 to transmit fluid away from the housing 11 to the tool tip 38. The fluid is typically saline used to cool and remove debris from the surgical site.

Figure 5:
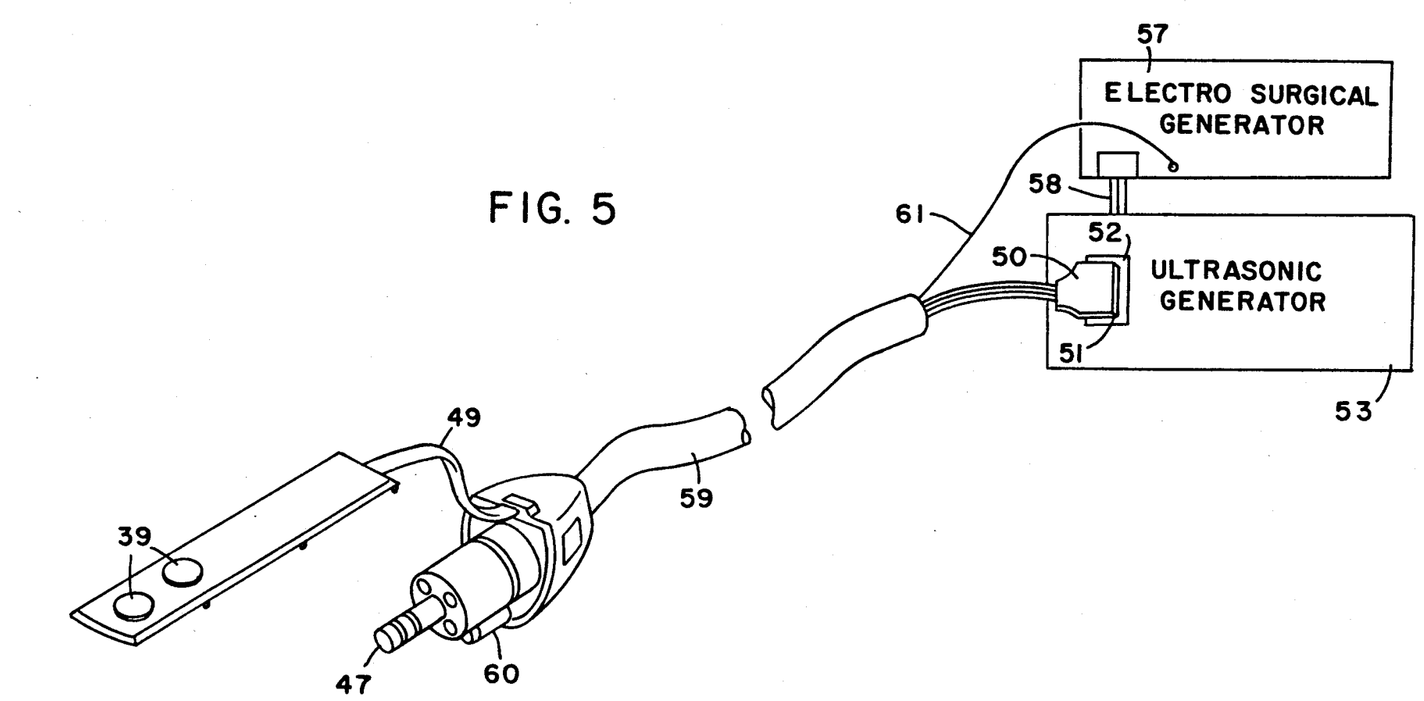
FIG. 5 is a perspective view similar to FIG. 2 but showing only the umbilical cord for the piezo ultrasonic and electrosurgical handpiece and the connections to the electrosurgical and ultrasonic generators.

A port 47 in FIGS. 2, 3 and 5 through the retainer 18 connects to a vacuum source (not shown) to provide suction at the tool tip 38 and the suction draws the coolant and debris up through the bore 43 and port 47 cooling the piezo transducer 15 thereabout in the stack 26 of elements 16. The angled juncture between the tool 36 and about the fastener 22 is at an obtuse angle so the flow of coolant and debris is free to pass therethrough.

A voltage potential between the feedback signal and the reference output indicates the characteristics of the stack 26 including the feedback crystal 27 in the handpiece 10. An adjustable resistance is located in series with the feedback signal and may be calibrated to a preset value so that the stack 26 can be used with any source of ultrasonic energy. Any tool 36 selected and designed to be interchangeably used with other tools of different lengths and configurations can be attached to the piezo ultrasonic and electrosurgical handpiece 10. Specifically, the adjustable resistance is adequate to calibrate for different tools so the stack 26 and source of energy may accommodate all the such interchangeable tools. The stroke at the tip 38 of the tool 36 is uniform, notwithstanding a different tool 36.

Figure 6:
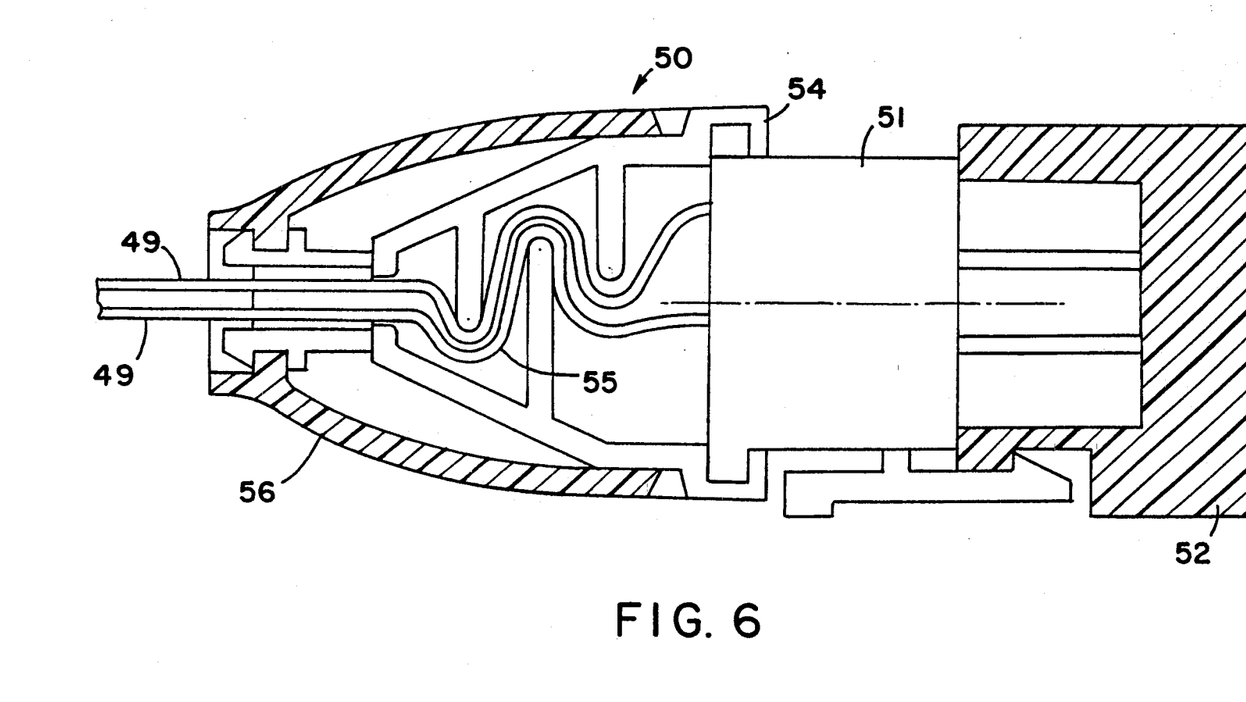
FIG. 6 is a perspective view shown exploded of the strain relief used to hold the flat ribbon cable.
Figure 7:
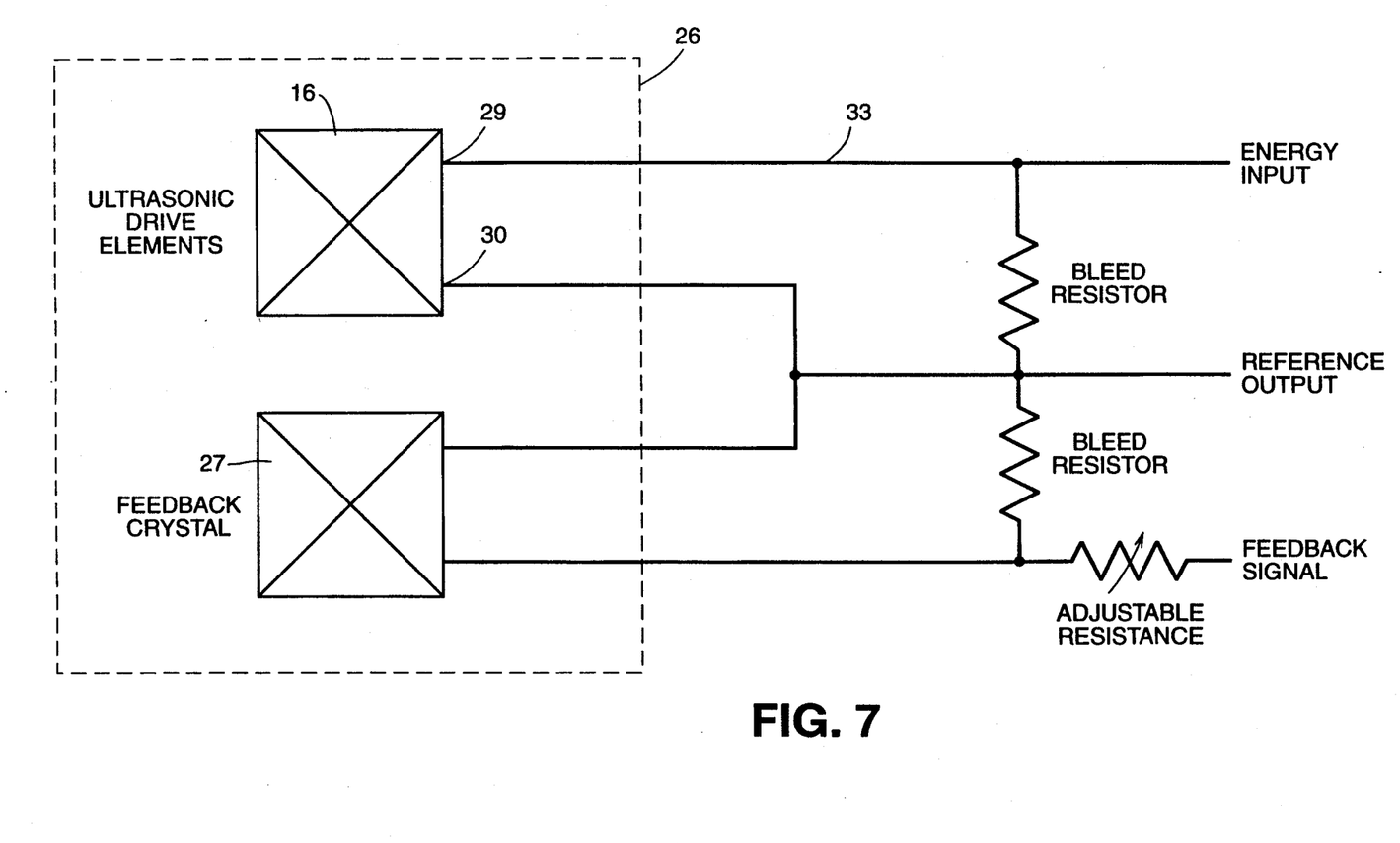
FIG. 7 is a schematic circuit diagram showing the relationship of the components in the piezo drive circuitry of the handpiece.

In FIG. 7 the stack 26 acts as a capacitor and bleed resistors are shown connected in parallel across and in circuit with the energy input of the elements, feedback signal and reference output, respectively, prevent accidental electrical discharge. Controls, in for example the form of switches 39, may be on an outside surface 48 of the housing 11 for managing the electrosurgical energy, the ultrasonic drive energy, and/or the irrigation. A flat ribbon of wires 49 connects the switches 39 and another ribbon of wires 49 connect the energy input of the elements, feedback signal and reference output. In particular, these are supplied to the handpiece 10 by two separate insulated three wire ribbon cables 49 best shown in FIG. 6. In one flat ribbon cable 49 the reference output is positioned amid the energy input and feedback output so that the capacitive coupling of the energy input and feedback output are minimized.

The insulated three wire ribbon cable 49 has a strain relief 50 in FIGS. 5 and 6 where it is connected to a connector block 51. A removable attachment receiving terminal 52 to an ultrasonic generator 53 has the wires of the ribbon cable 49 terminating at the connector block 51. A first slotted keeper 54 in FIG. 6 retains a serpentine length 55 of ribbon cable 49 when slid laterally over the serpentine length 55 and a second keeper 56 retains the first keeper 55. Specifically, the first and second keepers 55 and 56 conjugate with each other and connector block 51. The connector block 51 to terminate the wires is in circuit with the control switches 39. The ultrasonic drive energy and the reference output and feedback signal connect to the ultrasonic generator 53 and an electrosurgical generator 57 by a cable 58 from the connector block 51 to the standard footswicth jack on electrosurgical generator 57 when the connector block 51 is plugged into the receiving terminal 52 on the ultrasonic generator 53.

As shown in FIGS. 1, 2 and 5 a manifold 59 interconnects into the proximal end 13 and a floating fitting 60 disposed therebetween. The floating fitting 60 permits lateral movement of the fitting 60 to center and seal fluid flow to the irrigation channel 44 as best seen in FIG. 3. In FIG. 5 a single wire 61 is shown connected to the electrosurgical generator 57 to provide radio frequency energy to the handpiece 10 for electrosurgery at the tip 38.

What is claimed is:

1. A piezo ultrasonic and electrosurgical handpiece comprising:
    a housing being elongated along its axis and having a distal end and a proximal end and a passage therethrough;
    a piezo transducer having a plurality of elements supported within the housing and mounted along a plane generally transverse to the axis of the housing and the passage therealong;
    a retainer for the piezo elements, the retainer having a distal portion, intermediate portion and a proximal portion, the distal portion having a fastener positioned near the distal end of the housing, the proximal portion having an extended mandrel in the form of a shoulder bolt with proximally disposed threads, the intermediate portion attached to the housing with provisions for locating the retainer axial with respect thereto with decoupling therebetween;
    the piezo elements and a feedback crystal arranged in a stack of components, each component having a centrally located hole and an energy input and a reference output positioned axially apart from one another, the stack assembled on the shoulder bolt and positioned with the holes thereabout;
    an insulating sleeve disposed about the shoulder and sandwiched between the central openings of the stack and the shoulder of the bolt;
    a pair of insulators disposed about the retainer with the stack positioned between the insulators as a sandwich, one of the pair of insulators between the plane and the stack and the other insulator adjacent the threads and against the stack so an ultrasonic drive energy connected in circuit with the energy input of the elements, feedback signal and reference output in the stack are insulated by the sleeve and pair from the shoulder bolt;
    a washer located against the insulator and about the threads in position to apply axial but not torsional loads on the insulator and stack therebeneath;
    a clamping nut proximally located on the threads to hold the washer axially against the components on the shoulder bolt, the clamping nut including means for receiving an electrical source of electrosurgical energy, and
    electrical connections to the stack isolated from the clamping nut, the electrical connections including means for driving piezo elements, for receiving current flow through the piezo elements and for transmitting signals from the feedback crystal to cause controlled axial reciprocatory motion to be transmitted to the distal end of the retainer for conveyance to the fastener thereat and the plane of the retainer arranged at a node point of the axial reciprocatory motion.

2. The piezo ultrasonic and electrosurgical handpiece of claim 1 wherein a tool is connected to the fastener with complimentary connector and is held thereto for transmitting axial vibrations in the form of a predefined stroke therealong to a tip thereof.

3. The piezo ultrasonic and electrosurgical handpiece of claim 1 wherein the tool has an axis which is aligned with the axis of the retainer for the stack.

4. The piezo ultrasonic and electrosurgical handpiece of claim 1 wherein the housing passage has an inside wall and the retainer includes sealing provisions with respect to the inside wall of the housing, the retainer has an axial passageway therethrough allowing fluid flow to pass without fluid communicating with the electrical connections or the stack.

5. The piezo ultrasonic and electrosurgical handpiece of claim 1 wherein the fastener connects to a hollow tubular tool and having a bore therethrough located along an axis thereof, the bore in fluid communication with an axial passageway through the retainer.

6. The piezo ultrasonic and electrosurgical handpiece of claim 5 wherein an irrigation channel is provided within the housing and is segregated from the stack for conveying irrigation fluid at the distal end of the housing.

7. The piezo ultrasonic and electrosurgical handpiece of claim 6 wherein a flue conjugates with the distal end of the housing with the irrigation channel in fluid communication with the flue which is supported about the distal end of the housing concentric with respect to the tool for permitting irrigation fluid to pass within an annular space around the tool but inside of the flue to transmit fluid to the tool end away from the housing.

8. The piezo ultrasonic and electrosurgical handpiece of claim 7 wherein the passageway through the retainer is connected to a vacuum source to provide suction at the tool end.

9. The piezo ultrasonic and electrosurgical handpiece 1 wherein the juncture between the tool and the fastener is at an angle such that the axis of the passage through the retainer and an axis of the tool are at an obtuse angle.

10. The piezo ultrasonic and electrosurgical handpiece of claim 1 wherein washer is adapted to be held against twisting during tightening of the clamping nut to an axial preload that stretches the shoulder bolt so the stack is held under a predetermined compression.

11. The piezo ultrasonic and electrosurgical handpiece of claim 2 wherein a voltage potential between the feedback signal and the reference output is indicative of the particular feedback crystal in the handpiece and an adjustable resistance located in series with the feedback signal may be calibrated to a preset value so that the stack can be used with any source of ultrasonic energy.

12. The piezo ultrasonic and electrosurgical handpiece of claim 11 wherein the tool selected is interchangeable with other tools of different lengths and configurations and the adjustable resistance is capable of calibrating for those different tools so the stack and source of energy accommodate the tools and the stroke at the tip of the tool is uniform.

13. The piezo ultrasonic and electrosurgical handpiece of claim 2 wherein the stack acts as a capacitor and bleed resistors are connected in parallel across and in circuit with the energy input of the elements, feedback signal and reference output, respectively to provide electrical discharge.

14. The piezo ultrasonic and electrosurgical handpiece of claim 2 wherein controls are provided on an outside surface of the housing for controlling electrosurgical energy, ultrasonic drive energy, and irrigation.

15. The piezo ultrasonic and electrosurgical handpiece of claim 14 wherein the energy input of the elements, feedback signal and reference output are supplied to the handpiece by an insulated three wire ribbon cable with reference output amid the energy input and feedback output.

16. The piezo ultrasonic and electrosurgical handpiece of claim 15 wherein the insulated three wire ribbon cable has a strain relief for where it is connected to a connector block for removable attachment to an ultrasonic generator and the wires terminate at the connector block, a first slotted keeper for retaining a serpentine length of ribbon cable and a second keeper for retaining the first keeper.

17. The piezo ultrasonic and electrosurgical handpiece of claim 16 wherein the connector block to terminate the wires in circuit with the controls, with the ultrasonic drive energy, with the reference output and feedback signal is connected to an ultrasonic generator and an electrosurgical generator by a cable from the connector block to the electrosurgical generator when the connector block is plugged into a receiving terminal on the ultrasonic generator.

18. The piezo ultrasonic and electrosurgical handpiece of claim 1 wherein a manifold interconnects with the proximal end and a floating fitting disposed therebetween permits movement of the fitting to center and seal fluid flow to the irrigation channel.

19. A piezo ultrasonic and electrosurgical handpiece comprising:
  a housing being elongated along its axis and having a distal end and a proximal end and a passage therethrough, the housing passage has an inside wall;
  a piezo transducer having a plurality of elements supported within the housing and mounted along a plane generally transverse to the axis of the housing and the passage therealong;
  a retainer for the piezo elements, the retainer having a distal portion, intermediate portion and a proximal portion, the distal portion having a fastener positioned near the distal end of the housing, the proximal portion having an extended mandrel in the form of a shoulder bolt with proximally disposed threads, the intermediate portion attached to the housing with provisions for locating the retainer axial with respect thereto with decoupling therebetween, the retainer includes sealing provisions with respect to the inside wall of the housing;
  an irrigation channel within the housing and segregated from the stack for conveying irrigation fluid at the distal end of the housing;
  the piezo elements and a feedback crystal arranged in a stack of components, each component having a centrally located hole and an energy input and a reference output positioned axially apart from one another, the stack assembled on the shoulder bolt and positioned with the holes thereabout;
  an insulating sleeve disposed about the shoulder and sandwiched between the central openings of the stack and the shoulder of the bolt;
  a pair of insulators disposed about the retainer with the stack positioned between the insulators as a sandwich, one of the pair of insulators between the plane and the stack and the other insulator adjacent the threads and against the stack so an ultrasonic drive energy connected in circuit with the energy input of the elements, feedback signal and reference output in the stack are insulated by the sleeve and pair from the shoulder bolt;
  a washer located against the insulator and about the threads in position to apply axial but not torsional loads on the insulator and stack therebeneath;
  a clamping nut proximally located on the threads to hold the washer axially against the components on the shoulder bolt, the clamping nut including means for receiving an electrical source of electrosurgical energy, and
  electrical connections to the stack, the electrical connections including means for driving piezo elements, for receiving current flow through the piezo elements and for transmitting signals from the feedback crystal to cause controlled axial reciprocatory motion to be transmitted to the distal end of the retainer for conveyance to the fastener thereat and the plane of the retainer arranged at a node point of the axial reciprocatory motion and a tool is connected to the fastener with complimentary connector and is held thereto for transmitting axial vibrations in the form of a predefined stroke therealong to a tip thereof, the fastener connects to a hollow tubular tool and having a bore therethrough located along an axis thereof, the bore in fluid communication with an axial passageway through the retainer having a passageway therethrough allowing fluid flow to pass without fluid communicating with the electrical connections or the stack.

20. The piezo ultrasonic and electrosurgical handpiece of claim 19 wherein a flue conjugates with the distal end of the housing with the irrigation channel in fluid communication with the flue which is supported about the distal end of the housing concentric with respect to the tool for permitting irrigation fluid to pass within an annular space around the tool but inside of the flue to transmit fluid to the tool end away from the housing.

21. The piezo ultrasonic and electrosurgical handpiece of claim 20 wherein the passageway through the retainer is connected to a vacuum source to provide suction at the tool end.

22. The piezo ultrasonic and electrosurgical handpiece 19 wherein the juncture between the tool and the fastener is at an angle such that the axis of the passage through the retainer and an axis of the tool are at an obtuse angle.

23. The piezo ultrasonic and electrosurgical handpiece of claim 19 wherein a voltage potential between the feedback signal and the reference output is indicative of the particular feedback crystal in the handpiece and an adjustable resistance located in series with the feedback signal may be calibrated to a preset valve so that the stack can be used with any source of ultrasonic energy.

24. The piezo ultrasonic and electrosurgical handpiece of claim 23 wherein the tool selected is interchangeable with other tools of different lengths and configurations and the adjustable resistance is capable of calibrating for those different tools so the stack and source of energy accommodate the tools and the stroke at the tip of the tool is uniform.

25. The piezo ultrasonic and electrosurgical handpiece of claim 19 wherein controls are provided on an outside surface of the housing for controlling electrosurgical energy, ultrasonic drive energy, and irrigation.

26. The piezo ultrasonic and electrosurgical handpiece of claim 25 wherein the energy input of the elements, feedback signal and reference output are supplied to the handpiece by an insulated three wire ribbon cable with reference output amid the energy input and feedback output.

* * * * *